United States Patent [19]
Riese et al.

[11] Patent Number: 5,964,290
[45] Date of Patent: *Oct. 12, 1999

[54] CHEMICALLY INDUCED STIMULATION OF CLEAT FORMATION IN A SUBTERRANEAN COAL FORMATION

[75] Inventors: Walter C. Riese, Katy; Stephen V. Bross, Sugar Land, both of Tex.

[73] Assignee: Vastar Resources, Inc., Houston, Tex.

[*] Notice: This patent is subject to a terminal disclaimer.

[21] Appl. No.: 08/934,722

[22] Filed: Sep. 22, 1997

Related U.S. Application Data

[63] Continuation-in-part of application No. 08/594,725, Jan. 31, 1996, Pat. No. 5,669,444.

[51] Int. Cl.⁶ .......................... E21B 43/17; E21B 43/26; E21B 43/27; E21B 43/40
[52] U.S. Cl. .......................... 166/263; 166/245; 166/268; 166/271; 166/305.1; 166/308
[58] Field of Search .................................... 166/245, 263, 166/268, 271, 305.1, 308; 299/4, 5

[56] References Cited

U.S. PATENT DOCUMENTS

| | | | |
|---|---|---|---|
| 4,032,193 | 6/1977 | Drinkard et al. | 299/4 |
| 4,043,395 | 8/1977 | Every et al. | 166/268 X |
| 4,245,699 | 1/1981 | Steeman | 166/271 |
| 4,305,464 | 12/1981 | Masszi | 166/370 |
| 4,368,922 | 1/1983 | Hemphill et al. | 166/307 X |
| 4,391,327 | 7/1983 | De Carlo | 166/307 |
| 4,424,863 | 1/1984 | White | 166/268 |
| 4,537,252 | 8/1985 | Puri | 166/272 |
| 4,662,439 | 5/1987 | Puri et al. | 166/272 |
| 4,662,443 | 5/1987 | Puri et al. | 166/261 |
| 4,726,543 | 8/1988 | Pantermuuehl et al. | 62/28 |
| 4,747,642 | 5/1988 | Gash et al. | 166/256 |
| 4,756,367 | 7/1988 | Puri et al. | 166/263 |
| 4,765,407 | 8/1988 | Yuvancic | 166/268 |
| 4,833,170 | 5/1989 | Agee | 518/703 |
| 4,883,122 | 11/1989 | Puri et al. | 166/263 |
| 4,913,237 | 4/1990 | Kutas | 166/308 |
| 4,973,453 | 11/1990 | Agee | 422/190 |
| 4,993,491 | 2/1991 | Palmer et al. | 166/280 |
| 5,014,785 | 5/1991 | Puri et al. | 166/263 |
| 5,014,788 | 5/1991 | Puri et al. | 166/280 |
| 5,048,328 | 9/1991 | Puri | 73/153 |
| 5,085,274 | 2/1992 | Puri et al. | 166/252 |
| 5,099,921 | 3/1992 | Puri et al. | 166/266 |
| 5,133,406 | 7/1992 | Puri | 166/266 |
| 5,265,678 | 11/1993 | Grundmann | 166/308 |
| 5,332,036 | 7/1994 | Shirley et al. | 166/268 |
| 5,388,640 | 2/1995 | Puri et al. | 166/263 |
| 5,388,641 | 2/1995 | Yee et al. | 166/263 |
| 5,388,642 | 2/1995 | Puri et al. | 166/266 |
| 5,388,643 | 2/1995 | Yee et al. | 166/266 |

(List continued on next page.)

FOREIGN PATENT DOCUMENTS

| | | |
|---|---|---|
| 0181211 | 5/1986 | European Pat. Off. . |
| 1492238 | 11/1977 | U.S.S.R. . |
| 1492238 | 11/1977 | United Kingdom . |

OTHER PUBLICATIONS

Low temperature oxidation of brown coal. 3. Reaction with molecular oxygen at temperatures close to ambient by Philip D. Swann and David G. Evans, University of Melbourne, Parkville Victoria, 3052, Australia, Fuel vol. 58, Apr. pp. 276–280.

(List continued on next page.)

*Primary Examiner*—George Suchfield
*Attorney, Agent, or Firm*—F. Lindsey Scott

[57] ABSTRACT

A method for increasing the production of methane from a subterranean coal formation by chemically stimulating the formation of cleats in the formation to increase the rate of methane production from the formation by injecting an aqueous oxidant solution into the formation to stimulate the formation of cleats in the formation; and thereafter producing methane from the formation at an increased rate. Suitable oxidants include chlorine dioxide, metallic salts of perchlorate, chlorate, persulfate, perborate, percarbonate, permanganate, nitrate and combinations thereof.

20 Claims, 3 Drawing Sheets

U.S. PATENT DOCUMENTS

| | | | |
|---|---|---|---|
| 5,388,645 | 2/1995 | Puri et al. | 166/268 |
| 5,417,286 | 5/1995 | Palmer et al. | 166/308 |
| 5,419,396 | 5/1995 | Palmer et al. | 166/250 |
| 5,439,054 | 8/1995 | Chaback et al. | 166/252 |
| 5,454,666 | 10/1995 | Chaback et al. | 405/52 |
| 5,494,108 | 2/1996 | Palmer et al. | 166/308 |
| 5,566,755 | 10/1996 | Seidle et al. | 166/263 |
| 5,669,444 | 9/1997 | Riese et al. | 166/263 |
| 5,769,165 | 6/1998 | Bross et al. | 166/266 |
| 5,865,248 | 2/1999 | Riese et al. | 166/263 |

OTHER PUBLICATIONS

X–ray Studies of Coal Oxidation by Herbert Beall, Bradley J. Howard, John T. Vaughey, Worcester Polytechnic Institute in Energy 7 Fuels 1988, 2, 721–722.

Low Temperature Coal Weathering: Its Chemical Nature and Effects on Coal Properties by M.M. Wu, G.A. Robbins, R.A. Winschel & F.P. Burke, Consolidation Coal Company, Library PA 151229 in Energy 7 Fuels 1988, 2, 150–157.

Low–temperature oxidation of Victorian brown coal by S. Polat and I.J. Harris, University of Melbourne, Parkville, Victoria 3052 Australia in Fuel, 1984, vol. 63 May, pp. 669–672.

Low temperature oxidation of coals, Effects of pore structure and coal composition by Ryuichi Kaji, Yukio Hishinuma and Yoichi Nakamura, Hitachi Research Laboratory, Hitachi Ltd. 4026 Kuji–cho, Hitachi–shi, Ibaraki–ken, 319–12 Japan in Fuel, 1985 vol. 64, Mar., pp. 297–302.

Humic Acids from Coal Controlled Air Oxidation of Coals and Carbons at 150° to 400° by Louis D. Friedman and Corliss R. Kinney, Pennsylvania State College, State College, PA in Industrial and Engineering Chemistry, Dec. 1950, vol. 42, No. 12, pp. 2525–2529.

Chlorine Reactions with Organic Substances in Chlorine Chemistry, pp. 399–404.

Oxidations of coal by aqueous sodium hypochlorite by Frank R. Mayo and Norman A. Kirshen, SRI International, Menlo Park, CAL in Fuel 1979 vol. 58, Oct., pp. 698–704.

Aqueous Alkaline Liquefaction of Southeastern Lignite: Applications to Solution Mining, Recovery of Chemical Feedstocks and Chemical Comminution by Leon Y. Sadler, III and John C. Huang, University of Alabama©1982 by Marcel Dekker, Inc., pp. 353–375.

Engineering Analysis of In Situ Liquefaction of Coal by D.L. Wise and D.C. Augenstein, Dynatech R/D Company, Cambridge, Mass©1978 by Marcel Dekker, Inc., pp. 173–195.

Conversion of Coal to Simple Compounds by Franklin G. Parker, James P. Fugassi and H.C. Howard, Coal Research Laboratory, Carnegie Institute of Technology, in Industrial and Engineering Chemistry, vol. 47, No. 8 pp. 1586–1592.

Chemical Enhancement of Coal Seam Permeability by L.Y. Sadler and C. Chang, University of Alabama in SPE Image Library 16037.

Ozonization Studies of Coal Constitution by C. R. Kinney and L. D. Friedman, Division of Fuel Technology, Pennsylvania State College, in Ozonization Studies of Coal Constitution, vol. 74, Jan. 5, 1952, pp. 57–61.

Chemical Stimulation of Coalbed Methane Wells by Chiehming Chang, Thesis, University, Alabama pp. 20–83.

Oxidation of Carbonaceous Materials to Organic Acids by Oxygen at Elevated Pressures by R.C. Smith, R.C. Tomarelli and H.C. Howard, in The Journal of American Chemical Society, vol. LXI, Jul.–Dec. 1939 pp. 2398–2402.

The Modeling of Channel Formation During Underground Coal Gasification by B. Dinsmoor, Amoco Chemicals; J.M. Galland, France and T.F. Edgar, SPE–AIME, U. of Texas Austin in American Institute of Mining, Metallurgical and Petroleum Engineers, Inc., SPE 6185 pp. 1–12.

Chemical Constitution of Coal: As Determined by Oxidation Reactions, by H.C. Howard, Coal Research Laboratory, Carnegie Institute of Technology, Chapter 9 pp 346–377.

Water–Soluble Polycarboxylic Acids by Oxidation of Coal, by N.W. Franke, M.W. Kiebler, C.H. Ruof, T.R. Savich and H.C. Howard, Coal Research Laboratory, Carnegie Institute of Technology, Pittsburgh, PA in Industrial and Engineering Chemistry, Nov. 1952, pp. 2785–2792.

Feasibility Study of Coal–Fracture Enhancement Using Aqueous Sodium Hypochlorite, Final Report by A.H. Pelofsky, F.W. Dittman, Rutgers, The State University of New Jersey, Department of Chemical and Biochemical Engineering, Report of Department of Energy, No. DOE/MC/ 14771–1475.

SPE 20732 Paper entitled: "Enhanced Coalbed Methane Recovery", R. Puri and D. Yee, presented at the 65th Annual Technical Conference and Exhibition of the Society of Petroleum Engineers, New Orleans, LA, Sep. 23–26, 1990.

"Multicomponent High–Pressure Adsorption Equilibria on Carbon Substrates: Theory and Data", *Fluid Phase Equilibria*, 78 (1992) pp. 99–137; Elsevier Science Publishers, B.V., Amsterdam.

"Openhole Cavity Completions in Coalbed Methane Wells in the San Juan Basis", I.D. Palmer, Amoco Production Co.: M.J. Mavor, Resource Enterprises, Inc.; J.P. Seidle, J.L. Spitler, and R.F. Volz, Amoco Production Co.

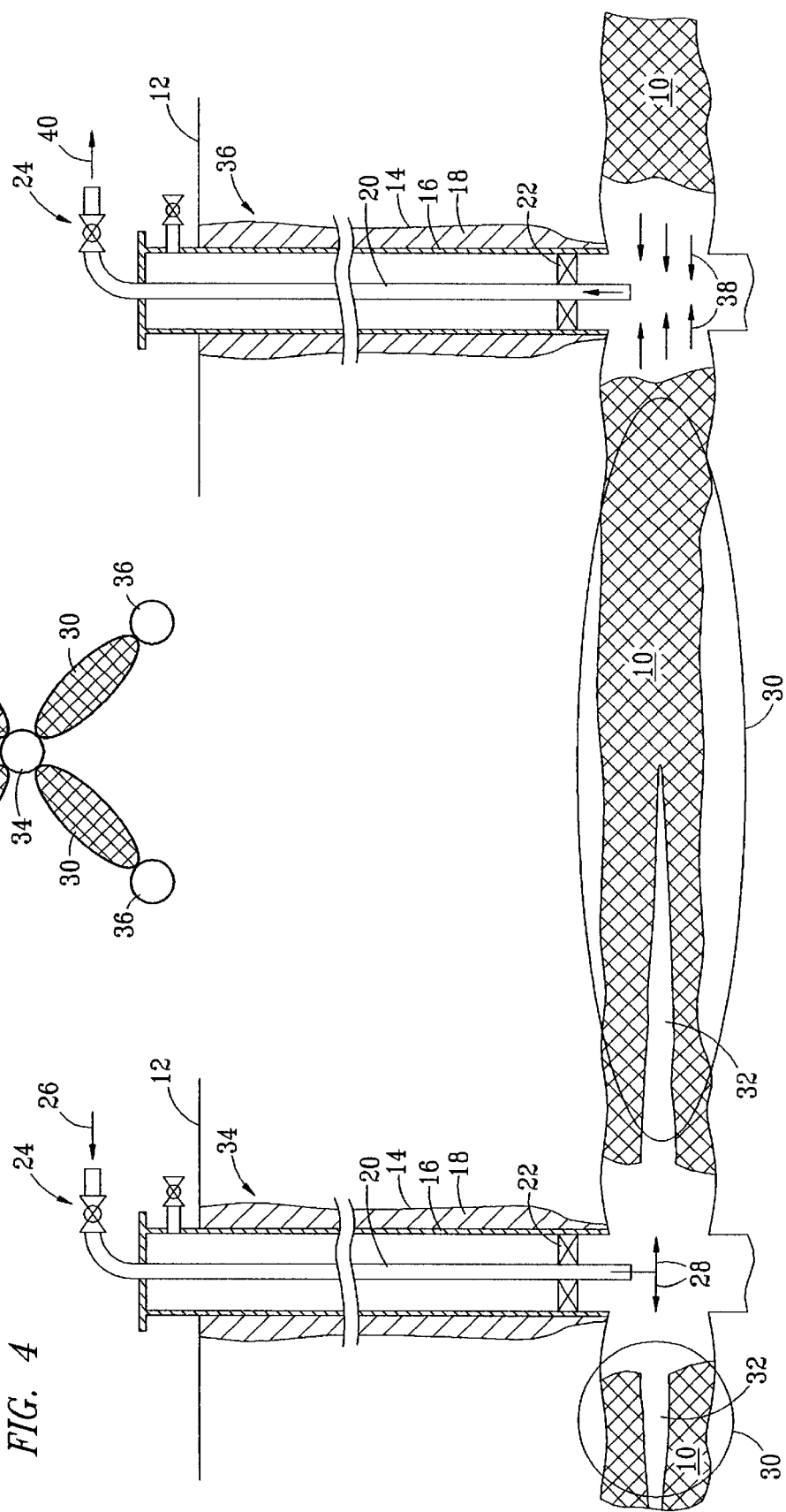

… … …

CHEMICALLY INDUCED STIMULATION OF CLEAT FORMATION IN A SUBTERRANEAN COAL FORMATION

CROSS-REFERENCE TO RELATED APPLICATION

This application is a continuation-in-part of U.S. Ser. No. 08/594,725, now U.S. Pat. No. 5,669,444, entitled "Chemically Induced Stimulation of Coal Cleat Formation" filed Jan. 31, 1996 by Walter C. Riese and Stephen V. Bross.

BACKGROUND OF THE INVENTION

1. Field of the Invention

This invention relates to methods for increasing the rate of production of methane from a subterranean coal formation by chemically stimulating the formation with an aqueous oxidizing solution to increase the production rate of methane from the formation.

2. Brief Description of the Prior Art

Substantial quantities of methane gas are found in subterranean coal formations. A variety of processes have been used in attempts to recover the methane from such coal formations more efficiently.

The simplest process is the pressure reduction process wherein a borehole is drilled into a coal formation from the surface and methane is withdrawn from the borehole by reducing the pressure to cause methane to be desorbed from and flow from the coal formation into the borehole and to the surface. This method is not efficient because coal formations are generally not extremely porous and the majority of the methane is generally not found in the pores of the coal formation but is absorbed or adsorbed to the coal. While methane can be produced from coal formations by this process, the production of methane is relatively slow.

In some coal formations, the natural permeability is sufficient to allow the removal of in situ water to permit the enhanced recovery of methane. In such formations, cleat systems developed during the coal bed diagenesis provide channel ways through which water and methane migrate to the production wells for removal. This removal of water or "de-watering" of the coal formations removes water from the channel ways and permits the flow of methane through the channel ways and to a production well at a greater rate.

Many coal formations do not have extensively developed cleat systems or have cleat systems which are not fully developed. These coal formations have very low permeability to water and gas and do not yield water or gas at significant rates. As a result, the water fills the channels, and the recovery of methane from such coal formations is difficult or impossible at significant rates. Such low permeability watercontaining coal formations may be either water saturated or less than fully water saturated. It appears that coal formations with better developed cleat systems may have been exposed to a diffusive oxidizing fluid of some type during the geologic past whereas coal formations with less developed cleat systems do not show evidence of exposure to an oxidizing fluid in the past.

The terms "absorbed" and "adsorbed" are used interchangeably in the discussion herein to refer to methane or other light hydrocarbons which are retained in or on the surfaces of carbonaceous or other materials.

Accordingly, continuing efforts have been directed to the development of methods for replicating the effects of the conditions in the better developed cleat system coal formations and increasing the production rate of methane from such formations.

SUMMARY OF THE INVENTION

According to the present invention, the rate of recovery of methane from a subterranean coal formation is increased by positioning at least one well from the surface into the formation; injecting an aqueous oxidant solution into the formation; maintaining the aqueous oxidant solution in the formation for a selected time to stimulate the formation or enhancement of a cleat system in the formation; and, producing methane from the formation at an increased rate.

Some suitable oxidants are hydrogen peroxide, ozone, oxygen, chlorine dioxide, water soluble metallic salts of perchlorate, chlorate, persulfate, perborate, percarbonate, permanganate, nitrate and combinations thereof.

The rate of production of methane from a subterranean coal formation penetrated by at least one injection well and at least one production well is increased by:

a) Injecting an aqueous oxidant solution containing at least one oxidant into the formation through the injection well; and b) Producing methane from the formation through the production well at an increased rate.

The present invention is effective to enhance methane recovery from coal formations.

BRIEF DESCRIPTION OF THE DRAWINGS

FIG. 4 is a schematic diagram of an injection well and a production well penetrating a subterranean coal formation from the surface wherein the coal formation has been fractured from the injection well.

FIG. 5 is a schematic layout of a 5-spot injection and production well pattern.

DESCRIPTION OF PREFERRED EMBODIMENTS

In the discussion of the Figures, the same numbers will be used throughout the specification to refer to the same or similar components.

Figure 1:
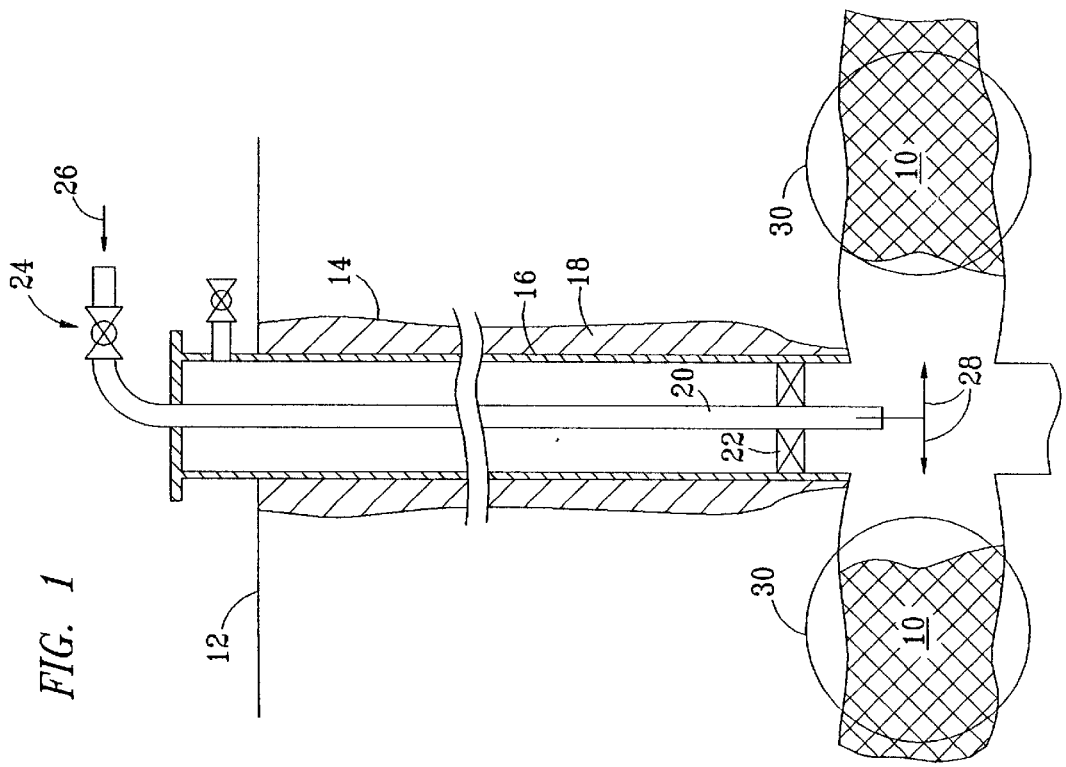
FIG. 1 is a schematic diagram of a well penetrating a subterranean coal formation from the surface.

In FIG. 1, a coal formation 10 penetrated from a surface 12 by a wellbore 14 is shown. The wellbore 14 includes a casing 16 positioned in the wellbore 14 by cement 18. While wellbore 14 is shown as a cased wellbore it should be understood that in the preferred embodiments shown in the Figures, cased or uncased wellbores could be used. Alternatively, the casing 16 could extend into or through the coal formation 10 with perforations through the casing in the coal seam providing fluid communication with the coal formation from the wellbore 14. The wellbore 14 extends into the coal formation 10 and includes a tubing 20 and a packer 22. The packer 22 is positioned to prevent flow between the outer diameter of the tubing 20 and the inner diameter of the casing 16. The wellbore 14 also includes equipment 24 adapted to inject a gaseous or liquid stream into the coal formation 10 or to recover a gaseous or liquid stream from the coal formation 10.

In the practice of the present invention, an aqueous oxidant solution is injected as shown by an arrow 26 through the tubing 20 into the coal formation 10 as shown by arrows 28. The zones treated are shown by circles 30. The aqueous oxidant solution is injected into the coal formation 10 for a selected time to enhance or stimulate the formation of a conductive, contiguous cleat system in the coal formation 10. The aqueous oxidant solution is injected for a period of time and in a quantity considered sufficient to increase the permeability of the coal formation 10 in the zones 30. After a selected period or after a selected amount of the aqueous oxidant solution has been injected, the well is shut in for a period of time which may be up to or greater than 24 hours. Typically, the well is shut-in until the pressure in the wellbore returns to the formation pressure and thereafter for at least 12 additional hours. Alternatively, a sufficient period of oxidant solution presence in the coal formation may have elapsed during the injection of the aqueous oxidant solution. The shut-in period allows for migration of the oxidant solution into the coal formation 10 to oxidize components of the coal formation 10 to enhance the cleat system in the coal formation 10. Subsequent to the shut-in period, water, methane or both may be recovered from the coal formation 10 to de-water the coal formation in the zones 30 and produce methane. The term "de-water" as used herein does not refer to the complete removal of water from the coal formation 10, but rather to the removal of sufficient water from the coal formation 10 to open passage ways in the cleat system in coal formation 10 so that methane can be produced through the passage ways from the coal formation 10.

The aqueous oxidant solution contains an oxidant selected from the group consisting of at least one of peroxide, ozone, oxygen, chlorine dioxide, water-soluble metallic salts of perchlorate, chlorate, persulfate, perborate, percarbonate, permanganate, nitrate and combinations thereof, or a group consisting of water soluble metallic salts of perchlorate, persulfate, perborate, chlorate, percarbonate, permanganate, nitrate and combinations thereof; of these the sodium and potassium salts of perchlorate, chlorate, persulfate, perborate, percarbonate, permanganate, nitrate and combinations thereof are preferred. Typically, the oxidant is used in concentrations up to the solubility limit of the oxidant in the aqueous oxidant solution. Preferred metallic salts are sodium and potassium salts. Such oxidants have been used as a fracturing fluid gel breaker in hydrocarbon-bearing formation fracturing applications and are commercially available.

In the embodiment shown in FIG. 1, a single well is used for injection of the aqueous oxidant solution to chemically enhance or stimulate the formation of a cleat system in the zones 30 to result in the release of formation water and an increase in the methane production rate from the coal formation 10. The term "increase" as used herein refers to a change relative to the untreated coal formation.

Figure 2:
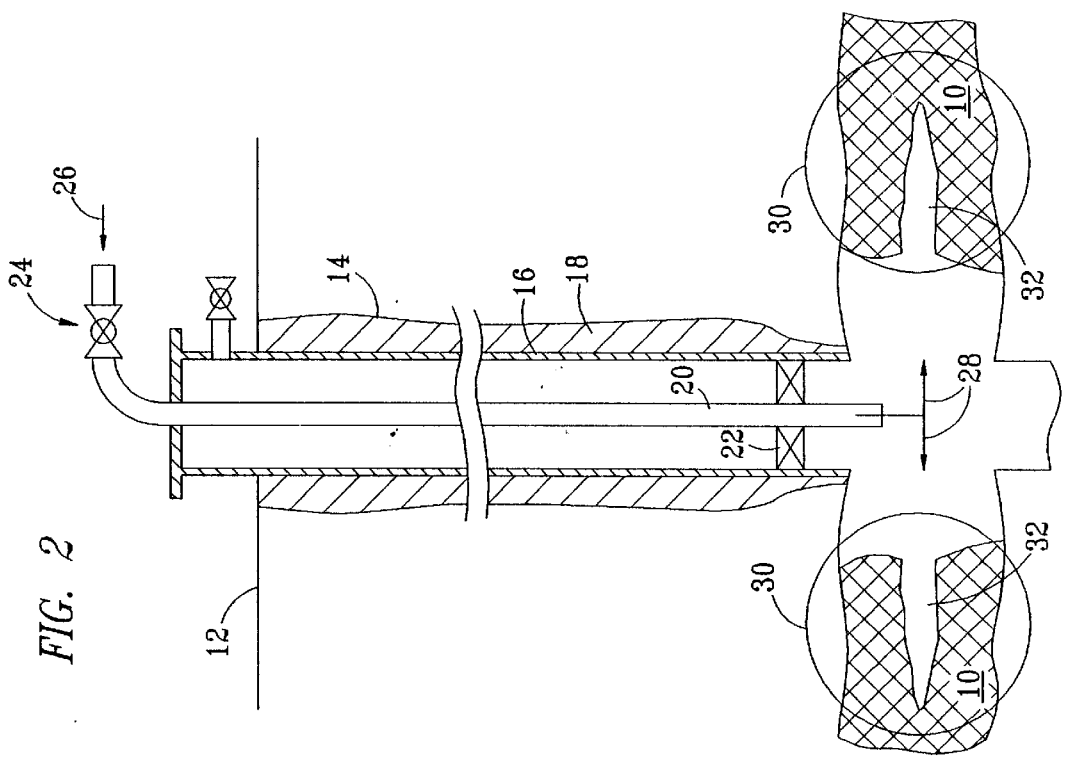
FIG. 2 is a schematic diagram of a well penetrating a subterranean coal formation from the surface wherein the coal formation has been fractured.

In FIG. 2, a similar embodiment is shown except that the coal formation 10 has been fractured by fractures 32. The operation of the well is basically the same as that shown in FIG. 1 except that the coal formation 10 has previously been fractured or is fractured by a fluid which may comprise the aqueous oxidant solution during at least part of the fracturing operation. For instance, it may be desirable to use a conventional fracturing application, if the coal formation 10 is sufficiently impermeable, as an initial stimulation method followed by the aqueous oxidant solution as a post-fracturing flush. The post-fracturing flush enhances cleat permeability throughout the areas contacting the fracture. In such instances, the well is desirably shut-in as discussed previously and the oxidants are selected from the same oxidant materials discussed previously. The fractures are formed in the coal formation 10 prior to injection of the oxidant solution. The oxidant solution could comprise the fracturing fluid if desired. The aqueous oxidant solution could also be injected above or below the fracture gradient (pressure) if desired.

Figure 3:
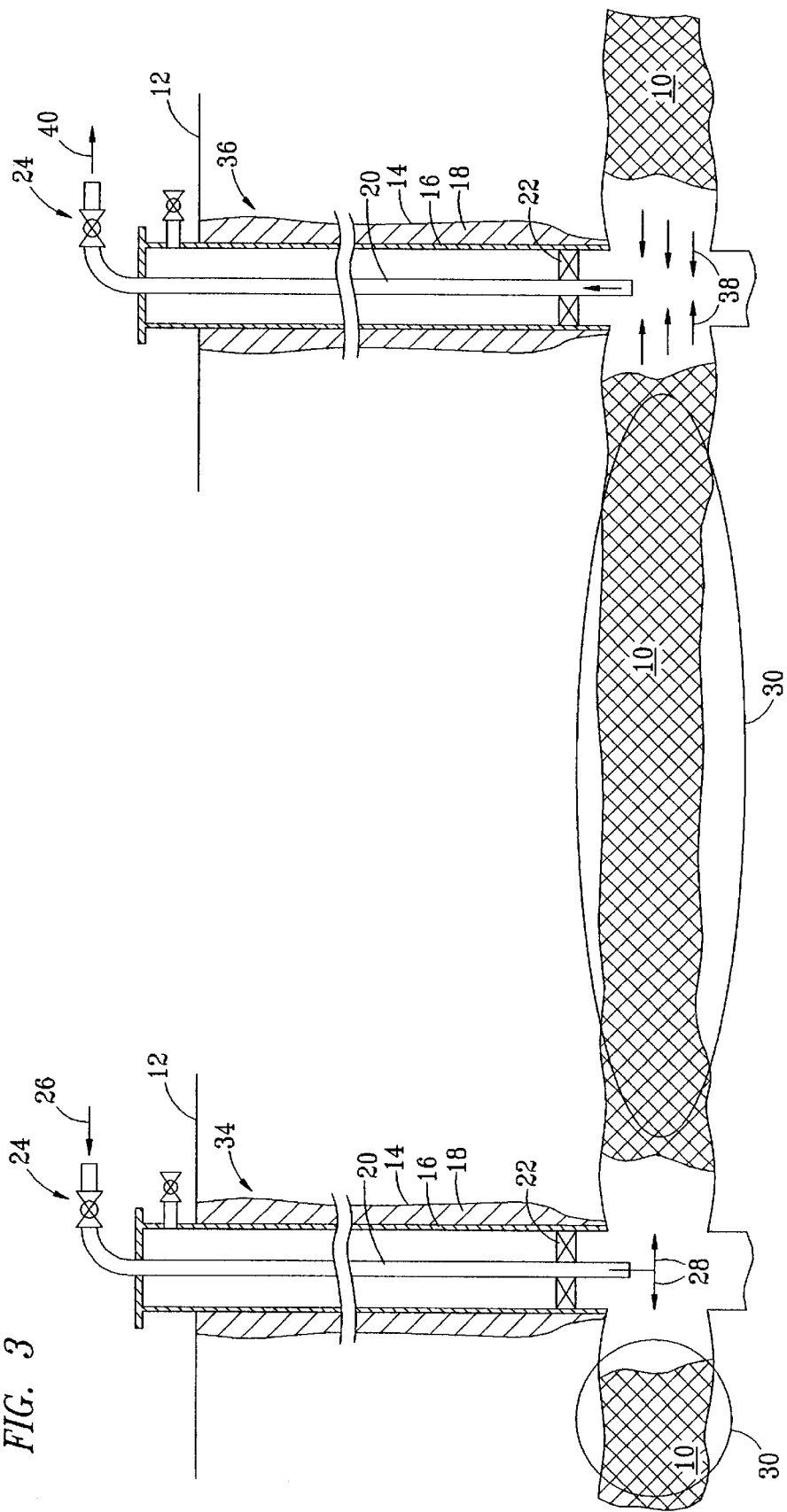
FIG. 3 is a schematic diagram of an injection well and production well penetrating a subterranean coal formation from the surface.

In FIG. 3, an injection well 34 and production well 36 penetrate the coal formation 10 from the surface 12. The injection well 34 is spaced apart from the production well 36 at a spacing based upon the characteristics of the particular coal formation and the like. According to the present invention, the aqueous oxidant solution described above is injected into the coal formation 10 through the injection well 34 as shown by the arrow 26 and the arrows 28 to treat the zones 30 which may extend from the injection well 34 in a generally circumferential direction, but generally extend preferentially toward a nearby production well 36 or production wells. The production well 36 is positioned to withdraw water and methane from the coal formation 10. The production of water and methane through the production well 36 causes the aqueous oxidant solution to migrate toward the production well 36. Desirably, injection of the aqueous oxidant solution is continued until an increased water volume is detected in production well 36 or until a desired increase in permeability or an increase in the volume of fluids produced is achieved. The increase in the permeability or volume of fluids produced from the production well 36 is indicative of the formation or enhancement of cleats in the coal formation 10 with a resulting increase in permeability so that additional quantities of fluids are released from the coal formation 10 for production as shown by arrows 38 through the production well 36 and a line 40. The arrows 38 are shown directed toward the production well 36 from both directions in contemplation that water will continue to be recovered at a lower rate from untreated portions of the coal formation 10.

The embodiment shown in FIG. 4 is similar to that shown in FIG. 3 except that the coal formation 10 has been fractured by fractures 32. Fractures 32 in the embodiment shown in FIG. 2 can be of substantially any extent. By contrast, in the embodiment shown in FIG. 4, the fractures 32 desirably extend no more than half way to the production well 36. Clearly, if the fractures 32 extend completely into the production well 36, it will be difficult to use any kind of fluid or gas drive between injection well 34 and production well 36. Desirably, the fractures extend no more than half the distance between the injection well 34 and the production well 36. The use of the aqueous oxidant solution with the fractures 32 is as discussed previously.

In FIG. 5, a 5-spot well arrangement is shown. Multiple well arrangements, such as 5-spot well arrangements, are useful in the practice of the present invention and may be used in a recurring pattern over a wide area. Such arrangements are well known to those skilled in the art and will be discussed only briefly. In the arrangement shown in FIG. 5, the aqueous oxidant solution is injected through the injection well 34 to treat the zones 30 to enhance the recovery of water and methane from the production wells 36. When the desired cleat formation or permeability increase has been achieved as evidenced by the production of fluids at an increased rate from production well 36, the injection of the aqueous oxidant solution is stopped and the injection well 34 can be converted to a production well. The area would then be produced through the original production wells and the converted injection well. The areas of enhanced cleat formation will increase the methane production rates and the ultimate methane recovery.

The method of the present invention is also useful as a pre-treatment for gas injection treatments to enhance the recovery of methane from the coal formation 10. The use of carbon dioxide, either alone or with other gases, to increase the production of methane from coal formations is well known. Similarly, the use of inert gases, such as nitrogen, argon and the like, to remove additional quantities of methane from coal formations by increasing the pressure in the formation and thereby removing additional methane as the methane partial pressure in the atmosphere in the coal seam is decreased are well known to those skilled in the art. The use of such processes requires that the formation be permeable to gas flow into or through the formation so that the methane can be recovered. The method of the present invention enhances the permeability of coal formations and may be used prior to the use of gas sweep or gas desorption treatments to enhance the recovery of methane.

Having thus described the present invention by reference to certain of its preferred embodiments, it is noted that the embodiments discussed are illustrative rather than limiting in nature and that many variations and modifications are possible within the scope of the present invention. Many such variations and modifications may be considered obvious and desirable by those skilled in the art based upon a review of the foregoing description of preferred embodiments.

We claim:

1. A method of increasing the rate of production of methane from a subterranean coal formation penetrated by at least one well, the method comprising:
    a) injecting an aqueous oxidant solution containing at least one oxidant selected from the group consisting of chlorine dioxide, water soluble metallic salts of perchlorate, perborate, chlorate, persulfate, percarbonate and permanganate, nitrate and combinations thereof into the formation;
    b) maintaining the aqueous oxidant solution in the formation for a selected time to stimulate the formation of cleats in the formation; and
    c) producing methane from the formation at an increased rate.

2. The method of claim 1 wherein the water soluble metal salts are salts of sodium or potassium.

3. The method of claim 1 wherein the aqueous oxidant solution comprises an aqueous solution of sodium or potassium perchlorate.

4. The method of claim 1 wherein the aqueous oxidant solution comprises an aqueous solution of sodium or potassium persulfate.

5. The method of claim 1 wherein the aqueous oxidant solution comprises an aqueous solution of sodium or potassium perborate.

6. The method of claim 1 wherein the aqueous oxidant solution comprises an aqueous solution of sodium or potassium percarbonate.

7. The method of claim 1 wherein the aqueous oxidant solution comprises an aqueous solution of sodium or potassium permanganate.

8. The method of claim 1 wherein the aqueous oxidant solution is injected into the formation through a first well; the first well is shut-in for a selected time; and thereafter, methane is produced from the first well at an increased rate.

9. The method of claim 1 wherein the formation has been fractured with fractures extending from the well prior to injection of the aqueous oxidant solution.

10. The method of claim 1 wherein the aqueous oxidant solution comprises a fracturing fluid injected at fracturing conditions to fracture the formation.

11. The method of claim 1 wherein said aqueous oxidant solution is maintained in the formation for at least 24 hours.

12. A method for increasing the production of methane from a subterranean coal formation penetrated by at least one injection well and at least one production well, the method comprising:
    a) Injecting an aqueous oxidant solution containing at least one oxidant selected from the group consisting of chlorine dioxide, water soluble metallic salts of perchlorate, chlorate, persulfate, perborate, percarbonate, permanganate, nitrate and combinations thereof into the formation through the injection well; and
    b) Producing methane from the formation through the production well at an increased rate.

13. The method of claim 12 wherein the metallic salts are sodium or potassium salts.

14. The method of claim 12 wherein the oxidant is present in an amount up to the solubility limit of the oxidant in water.

15. The method of claim 12 wherein the oxidant comprises sodium or potassium persulfate.

16. The method of claim 12 wherein the oxidant comprises sodium or potassium perchlorate.

17. The method of claim 12 wherein the oxidant comprises sodium or potassium perborate.

18. The method of claim 12 wherein the oxidant comprises sodium or potassium percarbonate.

19. The method of claim 12 wherein the oxidant comprises sodium or potassium permanganate.

20. The method of claim 12 wherein the oxidant comprises sodium or potassium nitrate.

* * * * *